(12) United States Patent
Hellkamp (10) Patent No.: US 9,930,957 B2
(45) Date of Patent: Apr. 3, 2018

(54) DENTAL DEVICES WITH LIQUID APPLICATOR

(71) Applicant: Martin E. Hellkamp, Roanoke, VA (US)

(72) Inventor: Martin E. Hellkamp, Roanoke, VA (US)

( * ) Notice: Subject to any disclaimer, the term of this patent is extended or adjusted under 35 U.S.C. 154(b) by 11 days.

(21) Appl. No.: 14/827,441

(22) Filed: Aug. 17, 2015

(65) Prior Publication Data
US 2016/0262531 A1   Sep. 15, 2016

(51) Int. Cl.
*A46B 11/00*   (2006.01)
*A61C 15/04*   (2006.01)
*A61C 15/02*   (2006.01)
*A61C 19/06*   (2006.01)

(52) U.S. Cl.
CPC ........ *A46B 11/001* (2013.01); *A46B 11/0041* (2013.01); *A61C 15/02* (2013.01); *A61C 15/046* (2013.01); *A61C 19/066* (2013.01)

(58) Field of Classification Search
CPC .. B43K 5/06; A46B 7/04; A46B 11/00; A46B 11/001; A46B 11/0041; A61C 15/046; A61C 15/02; A61C 19/066
USPC ........................................ 401/183, 278, 180
See application file for complete search history.

(56) References Cited

U.S. PATENT DOCUMENTS

| | | | | |
|---|---|---|---|---|
| 2,596,217 A * | 5/1952 | Dendy | ............... | A46B 11/0006 222/230 |
| 2,806,238 A * | 9/1957 | Wisey, Jr. | .......... | A46B 11/0017 222/394 |
| 3,094,130 A * | 6/1963 | Wiener | ............. | A46B 11/0017 222/394 |
| 3,337,893 A * | 8/1967 | Fine | ........................ | A46B 15/00 15/111 |
| 3,937,235 A * | 2/1976 | Broughton | ......... | A46B 11/0017 132/308 |
| 4,124,316 A * | 11/1978 | O'Rourke | .......... | A46B 11/0041 401/184 |
| 4,655,627 A * | 4/1987 | Bradley | ............. | A46B 11/0027 401/151 |
| 5,100,252 A * | 3/1992 | Podolsky | ........... | A46B 11/0027 401/174 |
| 5,346,324 A * | 9/1994 | Kuo | .................... | A46B 11/0055 401/141 |
| 5,908,257 A * | 6/1999 | Martin | ............... | A46B 11/0027 401/175 |
| 5,909,977 A * | 6/1999 | Kuo | .................... | A46B 11/002 401/146 |

(Continued)

*Primary Examiner* — David Walczak
(74) *Attorney, Agent, or Firm* — Bernard G. Pike; Pike IP Law, PLLC (57) ABSTRACT

Various dental devices are available for cleaning the mouth, gums and teeth. However, these dental devices may also cause abrasions to the mouth and/or gums. Dental devices may comprise a reservoir for storing a liquid and for application of the liquid to the mouth, teeth and/or gums. The liquid may be an antibacterial liquid, such as a hydrogen peroxide solution, a salt solution or a teeth whitening solution or gel, for example. An antibacterial liquid may be applied to prevent infection of the abrasions. The reservoir may be in a hollow handle of the dental device, such that the liquid may be easily pumped or moved from the reservoir to an outlet at the functional end that may cause the abrasions.

6 Claims, 7 Drawing Sheets

(56) References Cited

U.S. PATENT DOCUMENTS

| | | | | |
|---|---|---|---|---|
| 6,179,503 | B1* | 1/2001 | Taghavi-Khanghah | A46B 11/0058 |
| | | | | 401/145 |
| D641,522 | S* | 7/2011 | Nanda | D28/65 |
| 8,419,427 | B2* | 4/2013 | Effenberger | A61C 15/00 |
| | | | | 433/136 |
| 9,138,046 | B2* | 9/2015 | Jimenez | A46B 11/0006 |
| 2005/0135870 | A1* | 6/2005 | Frison | A46B 5/02 |
| | | | | 401/272 |
| 2007/0017546 | A1* | 1/2007 | Brown | A61C 15/046 |
| | | | | 132/323 |
| 2007/0110503 | A1* | 5/2007 | Glover | A46B 11/0024 |
| | | | | 401/134 |
| 2007/0157946 | A1* | 7/2007 | Lui | A61C 15/046 |
| | | | | 132/323 |
| 2009/0000048 | A1* | 1/2009 | Landfester | A46B 7/04 |
| | | | | 15/167.1 |
| 2009/0119859 | A1* | 5/2009 | Podolsky | A46B 17/04 |
| | | | | 15/167.1 |
| 2010/0223742 | A1* | 9/2010 | Kang | A46B 11/0017 |
| | | | | 15/22.1 |
| 2010/0284726 | A1* | 11/2010 | Ottaviani | A46B 11/0041 |
| | | | | 401/187 |
| 2011/0214240 | A1* | 9/2011 | Jimenez | A46B 11/001 |
| | | | | 15/167.1 |
| 2012/0183343 | A1* | 7/2012 | Kuo | A46B 7/04 |
| | | | | 401/171 |

* cited by examiner

DENTAL DEVICES WITH LIQUID APPLICATOR

RELATED APPLICATIONS

This patent application claims priority under 35 U.S.C § 119 to U.S. Provisional Patent Application No. 62/130,031 filed on Mar. 9, 2015.

FIELD OF THE INVENTION

Embodiments of dental devices may comprise a reservoir capable of retaining a liquid and dispensing the liquid when desired. Embodiments of the dental device comprise a handle, a reservoir, a functional end and an outlet for dispensing the liquid at the functional end.

BACKGROUND

There are hundreds of different shapes and sizes of what the industry refers to as "Dental Picks" or "Floss Picks" (hereinafter, "dental picks"). These devices consist of a small hand held single piece of plastic with a "U" or semi-circular head that has a piece of dental floss strung between the open ends of the "U". These devices are used to floss between the teeth while being held between the fingers of one hand. (See a typical dental pick FIG. 1). There are also many different shapes and sizes of toothbrushes. The term "dental devices" includes dental picks and toothbrushes.

A problem with the existing dental picks is that they all work on the concept of running a tight string (floss) between the teeth and down into the gums to free up loose debris and keep the gums pliable and free of foreign objects that can cause infection. However, most times, the pressure on the string up against the gums causes the gums to bleed. Even when gums do not show signs of bleeding, they are still exposed to small cuts from the floss; and are thus open for infection by foreign particles and bacteria. Brushing one's teeth vigorously with a toothbrush or using a sharp dental pick by the nature of the design may also result in similar injury and risk of infection to the gums and other parts of the mouth.

There exists a need for dental devices that comprise a reservoir of a liquid such as, but not limited to, an antibacterial, and means to apply the liquid to the functional end of the dental device and/or the mouth and gums of the user. There exists a further need for dental devices comprising a reservoir in the handle, wherein the reservoir is capable of retaining a liquid, and dispensing the liquid when desired to the gums or other portion of the mouth of a user.

SUMMARY

Embodiments include dental devices that are capable of storing a liquid and for application of the liquid to the mouth, teeth and/or gums. The liquid may be an antibacterial liquid, a hydrogen peroxide solution, a salt solution or a teeth whitening solution or gel, for example. The dental device comprises a functional end for cleaning some portion of the mouth, teeth or gums. The dental device comprises a reservoir for retaining the liquid, preferably the reservoir is in a hollow handle of the dental device, such that the liquid may be easily pumped or moved from the reservoir to an outlet at the functional end. The outlet may be defined on the functional end for dispensing the liquid, wherein outlet is in fluid communication with the reservoir, and the functional end comprises one of dental floss, a dental pick, and bristles. A force applied to the flexible cover of the handle compresses the reservoir to force liquid to be dispensed through the outlet.

In one embodiment, the dental device is a toothbrush. The toothbrush comprises a functional end, wherein the functional end comprises bristles, a handle connected to the functional end and a reservoir for retaining a liquid within the handle. The functional end has an outlet for dispensing the liquid within the reservoir onto the teeth, gums, or mouth of the user through a channel providing fluid communication between an inner volume of the reservoir and the outlet. In one particular embodiment, the reservoir is a replaceable reservoir cartridge installed within a recess defined in the handle.

Other aspects and features of embodiments of the dental devises, methods, and apparatuses will become apparent to those of ordinary skill in the art, upon reviewing the following description of specific, exemplary embodiments of the present invention in concert with the figures. While features may be discussed relative to certain embodiments and figures, all embodiments can include one or more of the features discussed herein. While one or more particular embodiments may be discussed herein as having certain advantageous features, each of such features may also be integrated into various other of the embodiments of the invention (except to the extent that such integration is incompatible with other features thereof) discussed herein. In similar fashion, while exemplary embodiments may be discussed below as system or method embodiments it is to be understood that such exemplary embodiments can be implemented in various systems and methods.

DESCRIPTION

Figure 1:
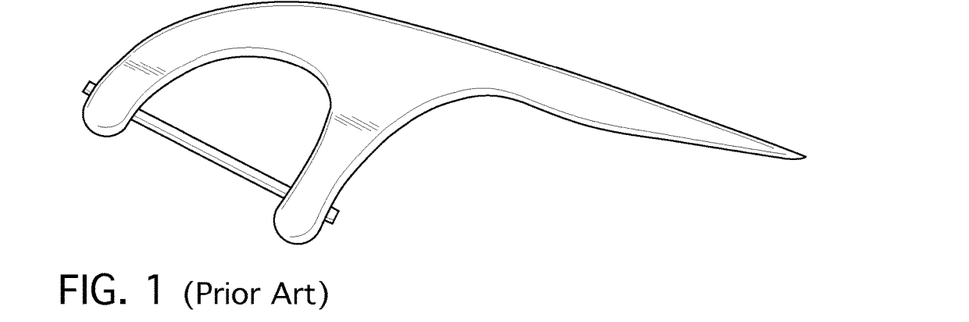
FIG. 1 depicts a conventional dental floss pick comprising a solid handle and two functional ends; one functional end comprising dental floss and the other functional end comprising a dental pick.
Figure 2A:
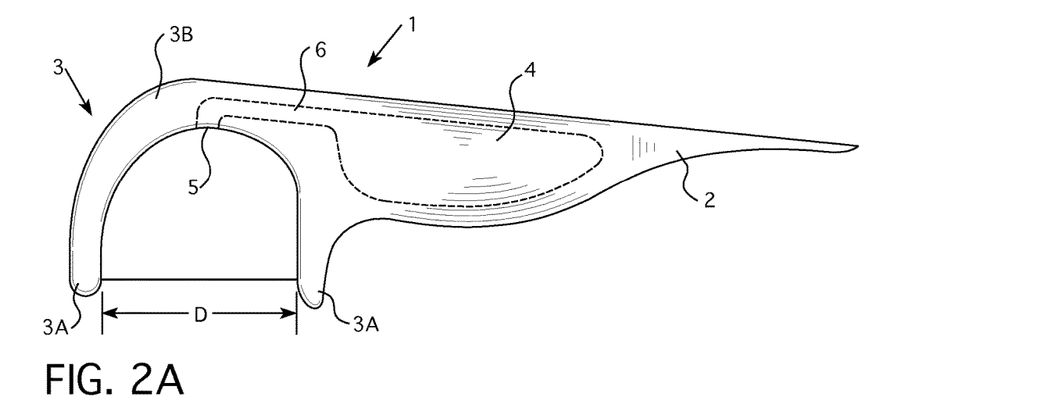
FIG. 2A depicts an embodiment of a dental floss pick comprising a functional end comprising dental floss, a hollow handle, a reservoir defined within the hollow handle for retaining a liquid and an outlet for dispensing the liquid, wherein outlet is in fluid communication with the reservoir.
Figure 2B:
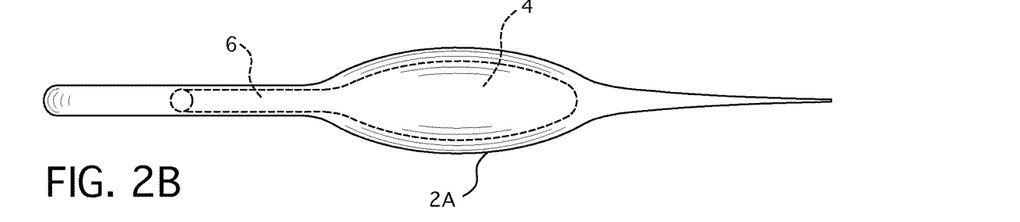
FIG. 2B is a top view of the embodiment of the dental floss pick in FIG. 2A.
Figure 2C:
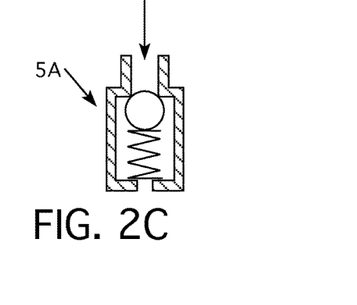
FIG. 2C depicts a ball check valve that may be inserted into the outlet to retard air intake into the reservoir and retard leaking of liquid from the reservoir when pressure is not applied to the hollow handle.
Figure 2D:
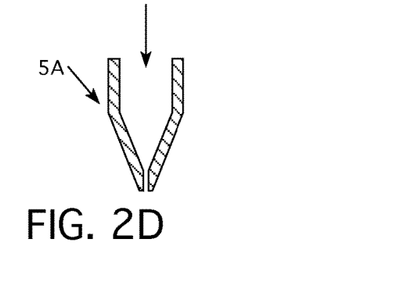
FIG. 2D depicts a duckbill check valve that may be inserted into the outlet to retard air intake into the reservoir and retard leaking of liquid from the reservoir when pressure is not applied to the hollow handle.
Figure 3A:
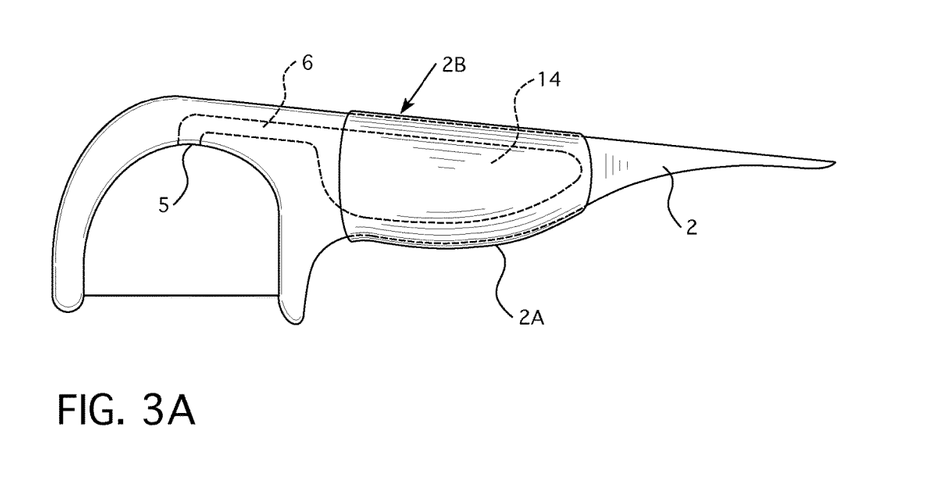
FIG. 3A depicts an embodiment of a dental floss pick comprising a functional end, a handle defining an inner chamber defined by a flexible cover, a reservoir within the inner chamber, and an outlet for dispensing the liquid.
Figure 3B:
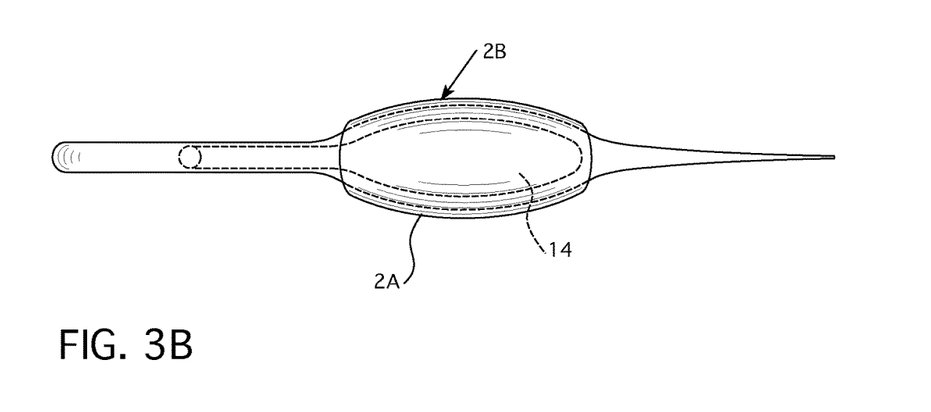
FIG. 3B is a top view of the embodiment of the dental floss pick of FIG. 3A.

A conventional dental nick is shown in FIG. 1. A typical dental pick is approximately 3 inches long with a head where the floss is mounted approximately a half inch. Embodiments of the dental floss pick may be similar in size to conventional dental pick, variations could also include different sizes and ergonomic design.

Embodiments are directed to dental floss picks, dental picks, toothbrushes, and other dental devices. In embodiments, the dental floss pick, dental pick, toothbrush, of other dental device 1 comprises a handle 2, a functional end 3, a reservoir 4 connected to or within the handle 2, and the reservoir 4 in fluid communication with an outlet on or adjacent to the functional end. The functional end of the dental device will define its uses. For a dental floss pick the functional end comprises a floss holder and floss. For a toothbrush, the functional end comprises a toothbrush head with bristles; and, for a dental pick, the functional end comprises a hook or a pick. In some embodiments, the dental device may comprise two functional ends which may be the same or different. For example, an embodiment of the dental device may comprise a first functional end comprising a floss holder and floss and a second functional end comprising a dental pick. Other combinations are possible as desired.

The reservoir 4 may be defined directly within the handle 2, wherein the wall of the handle also is the wall defining the inner volume of the reservoir 4 (See FIG. 2, for example). In such embodiments, the handle 2 may comprise a resilient body portion 2A such that a force exerted on the resilient body portion 2A of the handle 2 will reduce the volume of the reservoir 4 and force the contents out of the reservoir and toward the outlet 5. The outlet 5 may be a single aperture, a plurality of apertures or other nozzle design to spray or otherwise deposit the contents of the reservoir on the floss and/or mouth of the user. The dental device may further comprise a check valve 5A in communication with the outlet 5 such that the liquid in the reservoir 4 is forced through the outlet 5, the check valve 5A allows the liquid to exit the outlet 5 and to retard the flow of air to flow back into the reservoir 4. The check valve 5A may be any one way valve including, but not limited to, a ball check valve (as shown in FIG. 2C, for example), a duckbill check valve (as shown in FIG. 2C, for example), on umbrella valve, and a slit valve, for example.

In a specific embodiment, the dental device consists of a functional end, a handle, wherein the handle defines an internal reservoir 4 and an outlet 5 in fluid communication with the internal reservoir, and a check valve in the outlet. In such an embodiment, the internal reservoir 4 only has one inlet outlet to fill or force liquid out of the internal reservoir 4. For such a dental device, the method of manufacture comprises adding liquid through an outlet of a dental device, wherein the dental device consist of a functional end and a handle, wherein the handle defines an internal reservoir 4 and the outlet 5 in fluid communication with the internal reservoir; and inserting a Check valve into the outlet, wherein the check valve allows the liquid may exit the reservoir through the outlet if a force is applied to the handle of the dental device but retards air from entering the reservoir to replace the liquid. This embodiment may be specifically useful for a dental device wherein the handle is made of a resilient material, as described.

In some embodiments, the dental device may comprise a tube or tubes 6 providing fluid communication between the reservoir and the outlet. The tube or tubes 6 may be sized to provide the desired flow of the contents of the reservoir 4 to the outlet 5 when the reservoir 4 is under pressure from a force applied to it, such as a force of squeezing with fingers. The reservoir 4 and the reservoir may be conveniently located on the handle where a thumb or finger would normally grip the handle. The tube 6 leading to the outlet 5 may comprise the check valve 5A.

Figure 8A:
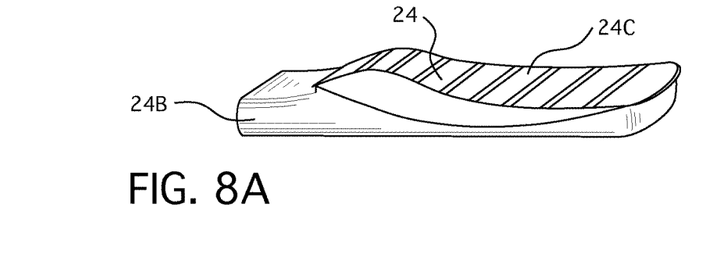
FIG. 8A depicts an embodiment of a portable or replaceable reservoir cartridge comprising a funneling shaped extension, wherein the funneling shaped extension comprises an outlet with a sealing material covering the outlet to prevent leakage of the liquid prior to inserting the cartridge in the cartridge recess defined in the handle.
Figure 8B:
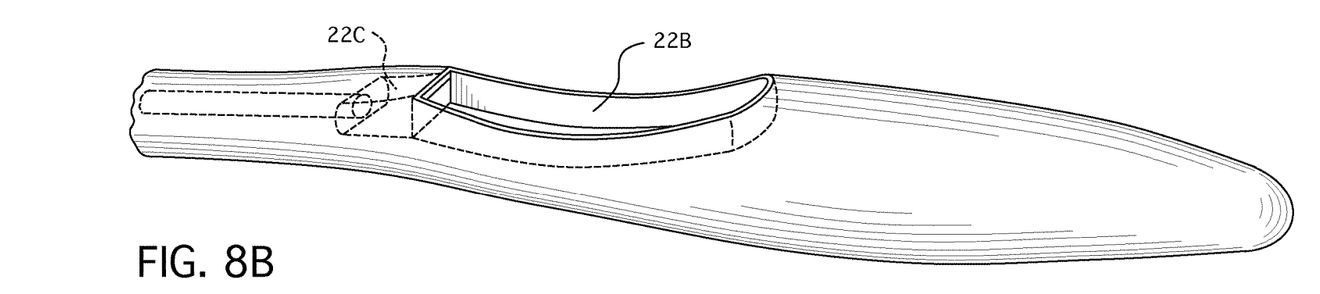
FIG. 8B is an enlarged view of the handle of the embodiment of the toothbrush of FIG. 8A comprising the flared portion of the channel with the connection tube recessed within the flared portion for breaking the sealing of the material after the funneling shaped extension is inserted within the flared portion.
Figure 8C:
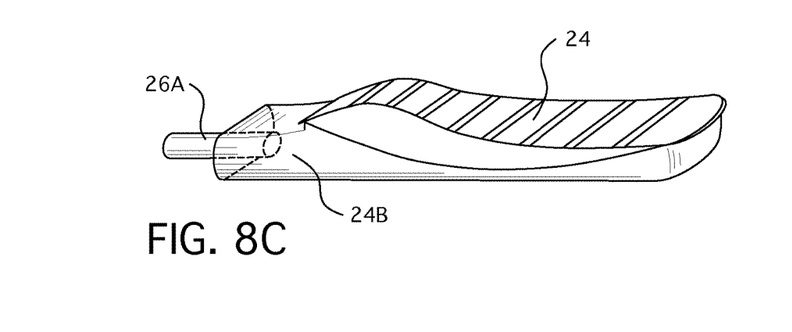
FIG. 8C depicts the connection tube aligned with the sealing material within the flared portion of the channel.

FIG. 8A shows the cartridge prior to being inserted into the cavity. The top part of the cartridge is made of a flexible rubber that is compressed like a primer pump to force liquid from inside the cartridge through the connection tube to the head of the toothbrush. FIG. 8B also shows the accepting cavity or compartment built into the toothbrush where the cartridge is inserted and then snaps into place by design. FIG. 8C also shows the connection tube inserted into the end of the cartridge and shows the end of the cartridge that accepts the connection tube insert. The accepting end of the cartridge is a rubber seal that unseals as the connection tube is inserted.

In the embodiment wherein the dental device is a dental floss (string) holder may be U-shaped or other shape having two floss holding posts 3A and a central portion 3B connecting and retaining the posts at a distance. The distance is greater than the width of a tooth and preferably at least two times the width of a human tooth. Floss may extend and be fastened to each of the posts 3A to allow the floss to be manipulated between the teeth of the user. The outlet may be defined in the central portion 3B or on one or both posts 3A such that the contents of the reservoir are deposited on floss extending between the posts or directly onto the mouth and gums.

The reservoir may be permanently integrated within the handle (as described above), may be refillable through an inlet (preferably an inlet comprising a cap for sealing the inlet); may be integrated into a replaceable cartridge that fits in a recess in the handle; or may be a separate internal reservoir within the handle. In an embodiment wherein the reservoir is a separate component within the handle (See FIGS. 3A, 3B, 4A, and 4B, for example), the handle surrounding the internal reservoir may comprise a flexible cover 2B, the flexible cover may comprise a resilient material such as rubber, a resilient plastic or polymeric material. In such embodiments, a force applied to the flexible cover 2B of the handle portion 2 moves the handle portion 2A and then the force is transferred to the internal reservoir 14 to the compress the internal reservoir 14 and move the liquid toward and through the outlet 5.

Figure 5A:
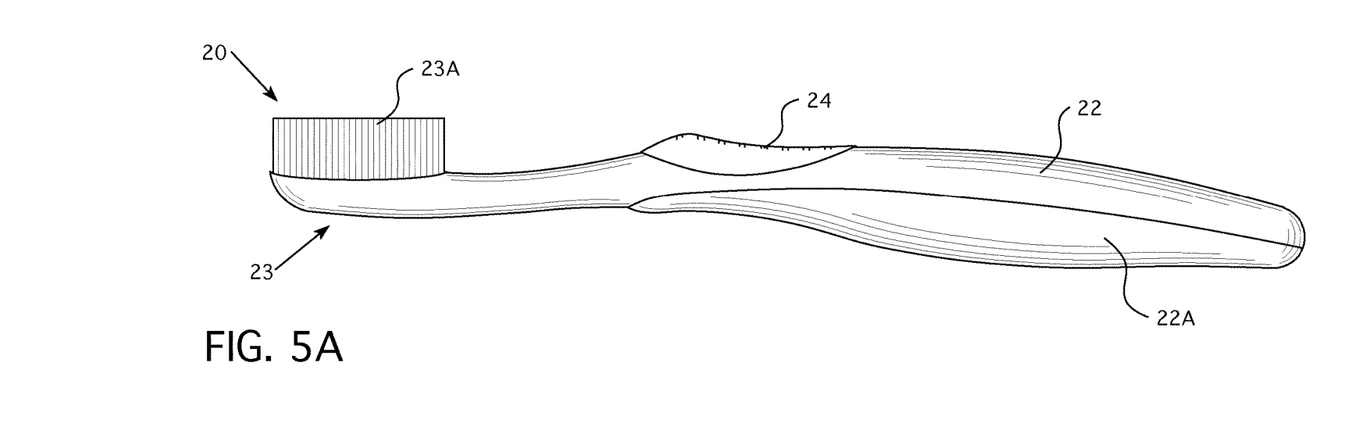
FIG. 5A depicts an embodiment of a toothbrush comprising a functional end, wherein the functional end comprises bristles, a handle, a reservoir for retaining a liquid and an outlet for dispensing the liquid, and a channel providing fluid communication between an inner volume of the reservoir and the outlet, wherein the reservoir is a replaceable cartridge installed within a recess defined in the handle.
Figure 6A:
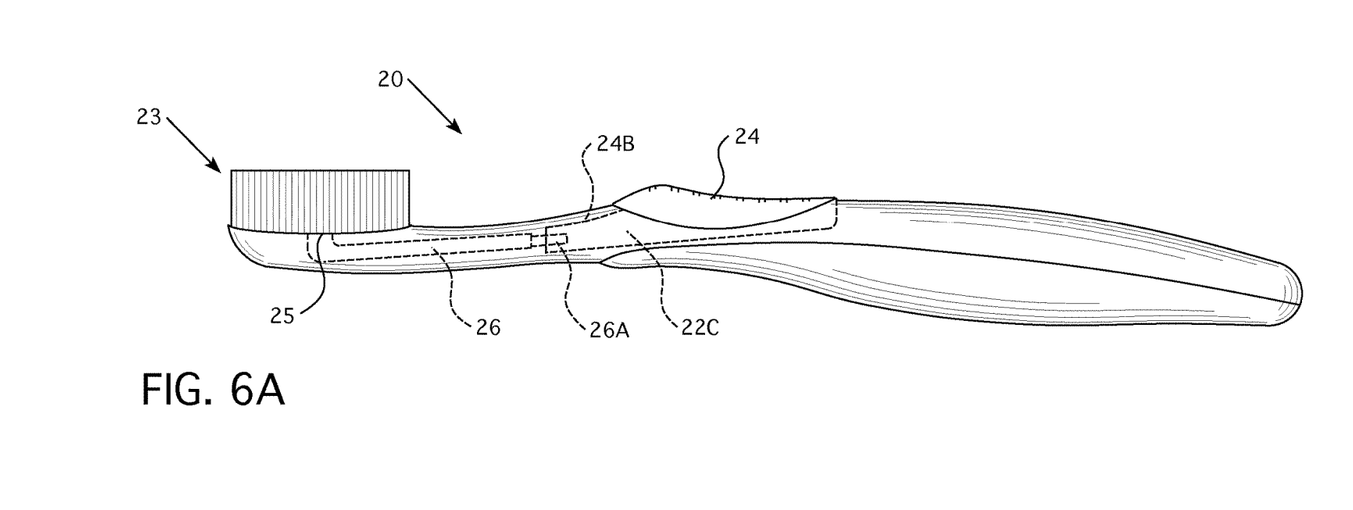
FIG. 6A depicts the embodiment of the toothbrush of FIG. 5A in a out away view showing the reservoir installed into the cartridge recess and connected to the channel by a connection tube, wherein the reservoir cartridge comprises an funneling shaped extension that extends into a flared portion of the channel to guide a reservoir outlet to the connection tube to provide a sealed connection between the reservoir and the channel.

A dental device, for example, the toothbrush 20 as shown in FIG. 5, comprises a reservoir wherein the reservoir is configured as a replaceable cartridge 24. A toothbrush may comprise a liquid delivery system built in that could spray liquid into the mouth as the user applied pressure to the handle with an inserted pump cartridge could revolutionize the teeth cleaning industry. The dental device 20 comprises a handle 22 with a recess 22B defined by the walls of the handle 22. The reservoir cartridge 24 may be complementary to the shape of the recess 22B in the handle 22. As shown in FIG. 6, the toothbrush 20 comprises a functional end 23 comprising bristles 23A. The toothbrush 22 comprises a handle 22 and a tube 26 providing fluid communication between the reservoir cartridge 24 and the outlet 25. In this embodiment, the tube 26 is connected to a connection tube 26A extending into the recess 226 defined by the walls of the handle 22. The connection tube 26A may be used to open an aperture 24A to allow the liquid within the cartridge 24 to flow into the tube 26 toward outlet 25. As the cartridge 24 is inserted into the recess 22B, the connection tube 26A may pierce the aperture 24A providing fluid communication to the outlet 25.

Figure 7A:
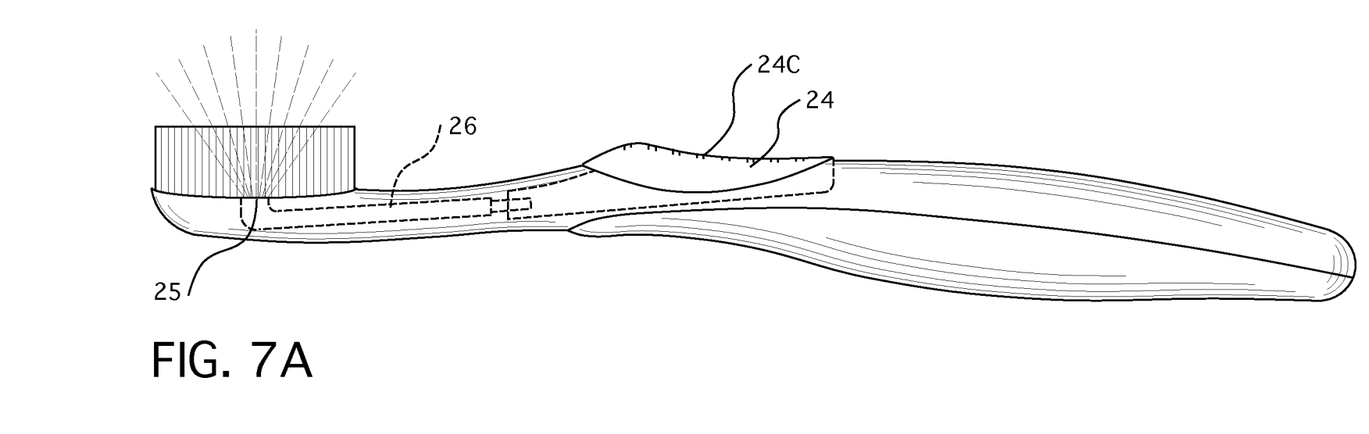
FIG. 7A depicts the embodiment of the toothbrush of FIG. 6 wherein a force has been applied to a flexible pump portion of the reservoir cartridge installed in cartridge recess defined in the handle thereby compressing the reservoir cartridge to force liquid into the tube and being dispensed through the outlet.

The insertable replaceable reservoir cartridge would contain the liquid that could be transferred while brushing the teeth. Once inserted, by pressing on the rubber pump while brushing the liquid is forced from the cartridge to the head of the toothbrush. The cavity built into the handle of the toothbrush that accepts the portable cartridge has a forward slot with a connection tube that penetrates the forward end of the cartridge once the cartridge is snapped into place (See FIGS. 6, 7, and 8, for example.) The connection tube is connected to a tube or an open canal that transfers the liquid from the cartridge to one or more outlet at the head of the tooth brush.

Figure 4A:
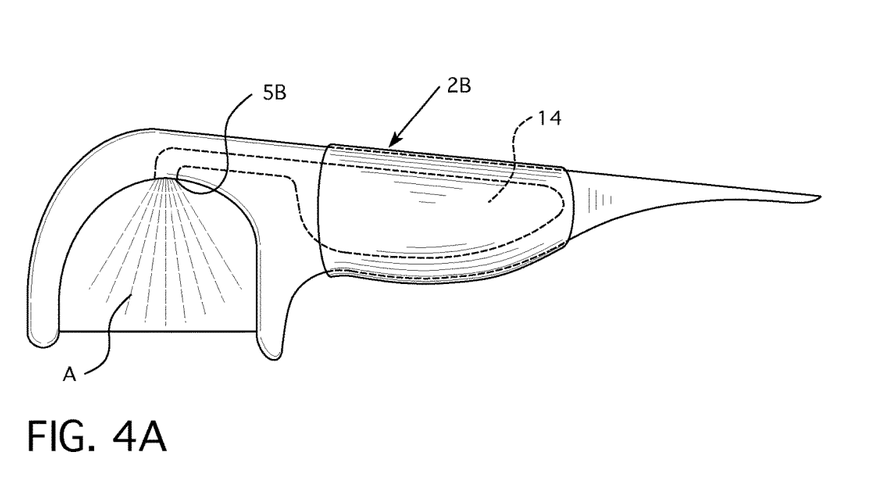
FIG. 4A depicts the embodiment of the dental floss pick of FIG. 3 wherein a force has been applied to the flexible cover of the handle thereby compressing the internal reservoir to force liquid into the tube and being dispensed through the outlet
Figure 4B:
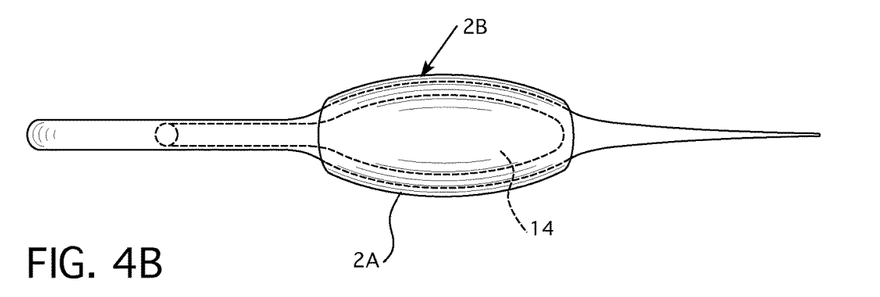
FIG. 4B is a top view of the embodiment of the dental floss pick of FIG. 4A.
Figure 4C:
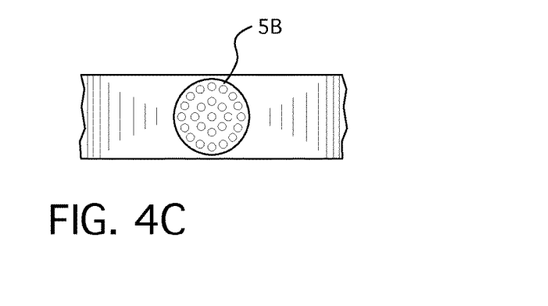
FIG. 4C depicts an enlarged view of the outlet, wherein the outlet has a cap defining apertures.
Figure 5B:
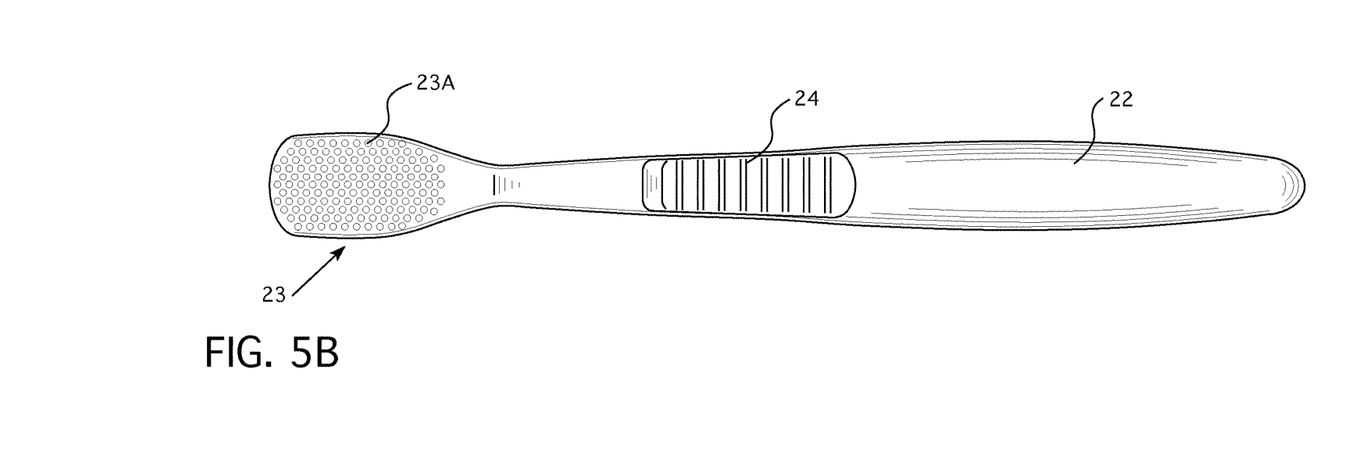
FIG. 5B is a top view of the embodiment of the toothbrush of FIG. 5A.

This new design of the dental pick is to have the handle of the pick made wider where the pick is generally held by the fingers. The wider area of the pick will be hollow (the pick "reservoir" see FIG. 2). The reservoir will be filled with anti-bacterial liquid. The reservoir part of the pick (where it is hollow) will be covered with pressure sensitive flexible covering material made into the handle of the pick, (rubber substance similar in concept to a squeeze ball or a finger primer for a small engine; see FIGS. 3A and 3B). The purpose of the flexible cover is to allow pressure from the fingers to force the liquid in the reservoir to flow. The reservoir of the handle will have one (or multiple) canals that lead to the head of the floss pick where the ends of the canals will be open (see FIGS. 4A, 4B, and 4C). The purpose of the open ended canal(s) is to allow liquid stored in the reservoir, when pressure is applied to the flexible cover, to flow to the head and deliver a spray of liquid in the vicinity of the actual floss (a similar affect as a squirt gun when the trigger is pulled, see FIGS. 5A and 5B). With the use of the Steri-Pick all areas of the gums are now treated while using the loss pick with anti-bacteria liquid keeping the gums healthier.

Figure 6B:
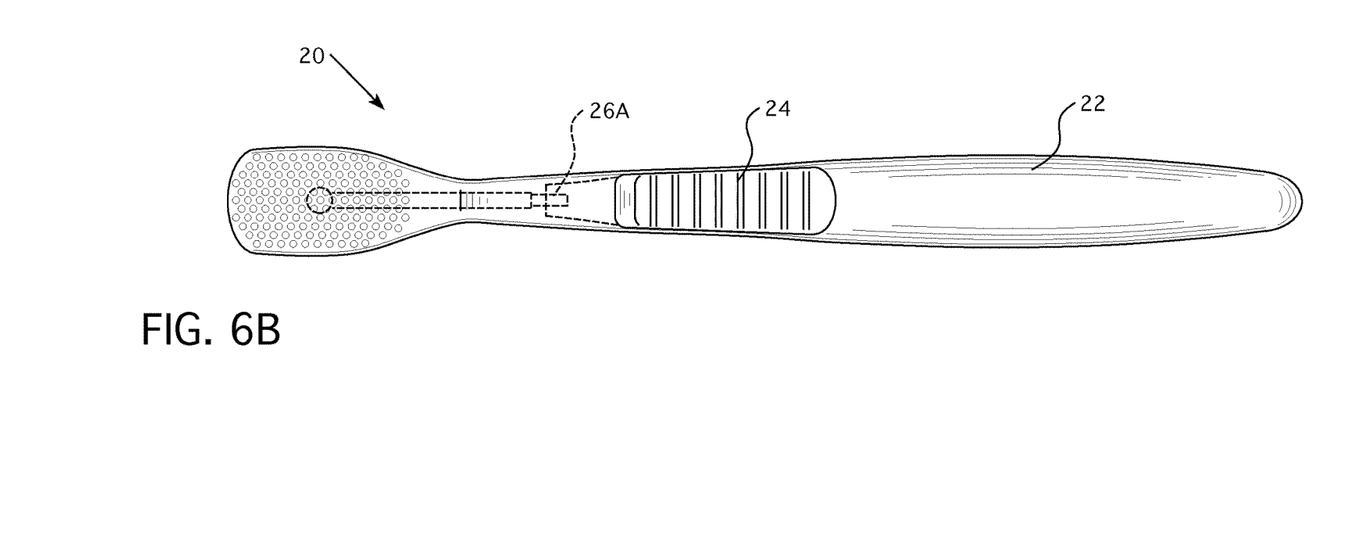
FIG. 6B is a top view of the embodiment of the toothbrush of FIG. 6A.

FIG. 6A depicts the embodiment of the toothbrush 20 of FIG. 5A in a cut away view showing the reservoir cartridge 24 installed into the cartridge recess 22B (See FIG. 8B) and connected to the channel 26 by a connection tube 26A, wherein the reservoir cartridge 24 comprises an funneling shaped extension 24B that extends into a flared portion 22C of the channel 26 to guide a reservoir outlet 24A to the connection tube 26A to provide a sealed connection 24A between the reservoir cartridge 24 and the channel. FIG. 6B is a top view of the embodiment of the toothbrush 20 of FIG. 6A.

Figure 7B:
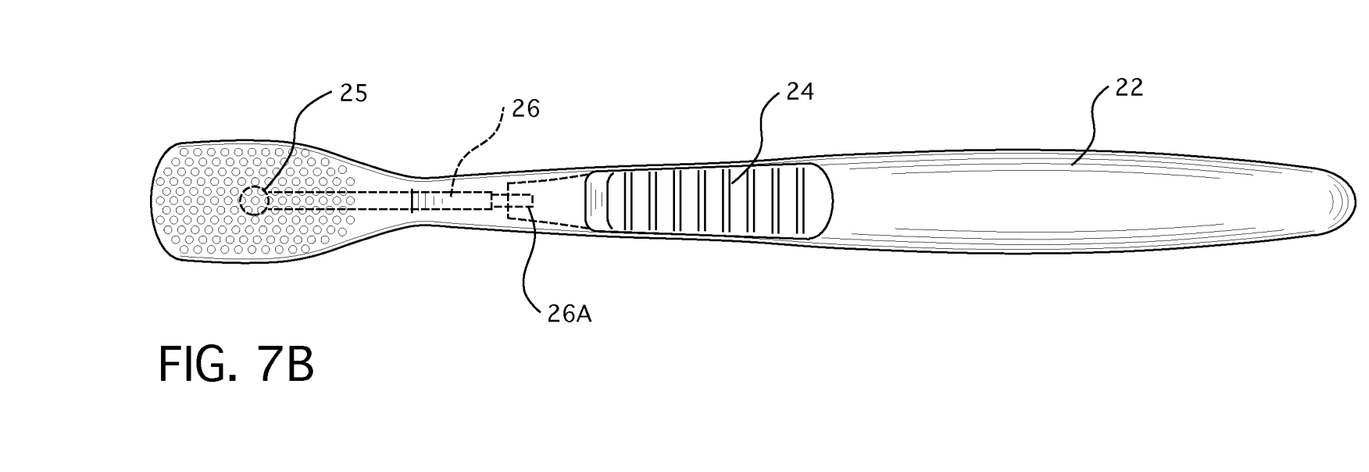
FIG. 7B is a top view of the embodiment of the toothbrush of FIG. 7A.

FIG. 7A depicts the embodiment of the toothbrush 20 of FIG. 6 wherein a force has been applied to a flexible pump portion 24C of the reservoir cartridge 24 installed in cartridge recess 22B defined in the handle 22 thereby compressing the reservoir cartridge 24 to force liquid into the channel 26 and being dispensed through the outlet 25. FIG. 7B is a top view of the embodiment of the toothbrush 20 of FIG. 7A.

Figures 8D, 8E:
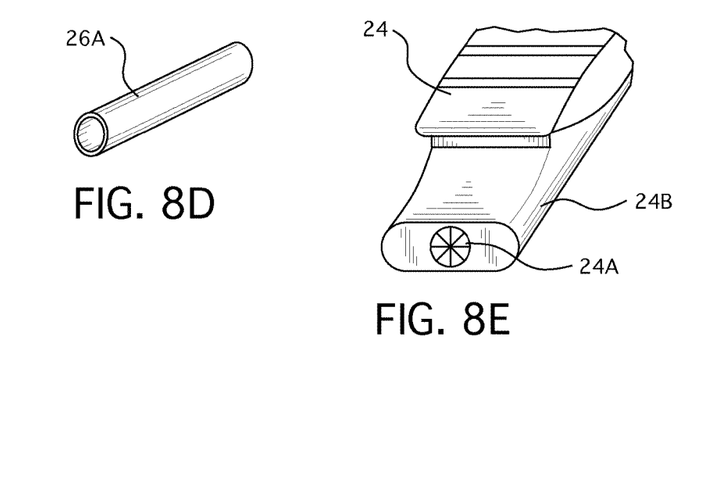
FIG. 8D depicts an embodiment of the connection tube.
FIG. 8E depicts an embodiment of the end of the reservoir cartridge with the sealing material on the end of the funneling shaped extension.

FIG. 8A depicts an embodiment of a portable or replaceable reservoir cartridge 24 comprising a funneling shaped extension 24B, wherein the funneling shaped extension 24B comprises an outlet 24A with a sealing material covering the outlet 24A to prevent leakage of the liquid prior to inserting the reservoir cartridge 24 in the cartridge recess 22B defined in the handle 22. FIG. 8B is an enlarged view of the handle 22 of the embodiment of the toothbrush 20 of FIG. 7A comprising the flared portion 22C of the channel 26 with the connection tube 26A recessed within the flared portion 22C for breaking the sealing of the material after the funneling shaped extension 24B is inserted within the flared portion 22C. FIG. 8C depicts the connection tube 26A aligned with the sealing material within the flared portion 22C of the channel 26. FIG. 8D depicts an embodiment of the connection tube 26A in the shape of a cylinder. In some embodiments, the connection tube 26A may be pointed to assist in inserting the connection tube 26A in the outlet 24A and piercing the sealing material. The connection tube 26A may further include a sealing device such as an o-ring to provide a sealing connection. FIG. 8E depicts an embodiment of the end of the reservoir cartridge 24B with the sealing material on the outlet 24A of the funneling shaped extension 24B.

Variations of the type of liquid stored in the reservoir. For instance, the reservoir could contain a teeth whitening agent as well as anti-bacteria liquid. The reservoir could be changed to contain a gel that would coat the gums and teeth. In one embodiment, the liquid is a hydrogen peroxide solution having a concentration in the range of 0.5% to 5% by weight, in another embodiment, the liquid is a hydrogen peroxide solution having a concentration in the range of 0.2% to 3% by weight. In another embodiment, the liquid comprises a hydrogen peroxide solution having a concentration in the range of 0.5% to 5% and sodium chloride solution in a concentration range of 0.5% to 2% by weight in water. In another embodiment, the replaceable cartridges comprise a teeth whitening composition. The dental device comprises a plurality of replaceable reservoir cartridges wherein the replaceable cartridges comprise different liquids. For example, the plurality of replaceable reservoir cartridges include a replaceable reservoir cartridge comprising as hydrogen peroxide solution having a concentration in the range of 0.2% to 3% by weight in water and a second replaceable reservoir cartridge comprising a tooth whitening product or gel. A tooth whitening product comprises a greater concentration of hydrogen peroxide than the antibacterial product described above. In a further embodiment, the plurality of replaceable reservoir cartridges further comprise a sodium chloride solution in a concentration range of 0.5% to 2% by weight in water.

In the embodiments described in the FIGs., the dental devices comprise a reservoir with at least one wall made of compressible material such that the reservoir may be compressed to reduce its volume and force liquid out of the reservoir. In other embodiments of the dental device, the reservoir could have a trigger delivery mechanism or other type of pump device that would cause the liquid to flow. The liquid delivered from the reservoir to the functional end could also be cause by a flexible head of the dental device creating openings in the ends of the canal or canals that allow liquid to flow when the head is distorted by being flexed up against teeth or gums. The reservoir could also lie designed into the functional end of the dental device instead of within the handle.

Because there are also teeth cleaning devices on the market that come in the form of small brushes, the Steri-pick concept can also be applied to the handles of the brush devices to be designed with a reservoir and liquid delivery system to the brush area that comes in contact with teeth and gums.

Some dental pick devices on the market come in the form of a larger handle similar to a tooth brush. This design can also be incorporated into a these types of pick devices. In other embodiments of the dental device, the other dental devices could incorporate the replaceable reservoir cartridges as described above in relation to the toothbrush.

Embodiments of the dental devices could also be made to be a refillable permanent reservoir built into the toothbrush instead of portable cartridge inserts. Also, the portable cartridge inserts could be made to be refillable by squeezing the pump top and submerging the receiving end into liquid then releasing the pump which would cause the cartridge to draw in liquid. Once re-filled, the cartridge could again be inserted into the toothbrush. The liquids that could be contained within the cartridge could be anything from teeth whitening ingredients to gum treatments to disinfectants to teeth sensitive materials.

The replaceable reservoir cartridges may be removed from the dental device and replaced with another replaceable reservoir cartridge containing the same or a different liquid. As used herein, "replaceable" means that the reservoir cartridges may be inserted, used and removed from the dental device by a typical consumer without special skills, the replaceable cartridge is retained in the dental device by a snap lock structure, a friction connection, thumb screw or wing nut, or other connector that does not require special tools or skills to remove and in not a more permanent connectors such as rivets or permanent glue, for example.

The embodiments of the described methods and dental devises are not limited to the particular embodiments, components, method steps, and materials disclosed herein as such components, process steps, and materials may vary. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A toothbrush system, comprising
   a toothbrush, comprising:
      a functional end, wherein the functional end comprises bristles;
      a handle connected to the functional end, wherein the handle defines a cartridge recess and a flared portion of the recess defined by walls of the handle;
      an outlet for dispensing the liquid in the functional end;
      a connection tube protruding from the functional end into the flared portion of the recess;
      a tube providing fluid communication between the connection tube and the outlet; and
   a first replaceable reservoir cartridge retaining a first liquid, the first replaceable reservoir cartridge comprising a first funneling shaped extension, a first outlet defined in a forward end of the first funneling shaped extension, a first sealing material covering the first outlet, and a first pump for displacing the first liquid into the functional end of the toothbrush, wherein the first replaceable cartridge is removably inserted into the cartridge recess with the first funneling shaped extension inserted into the flared portion of the recess and the connection tube extending through the first sealing material into the first funneling shaped extension.

2. The toothbrush system of claim 1, wherein the first liquid is a sodium chloride solution in a concentration range of 0.5% to 2% by weight in water.

3. The toothbrush system of claim 1, comprising a check valve in communication with the connection tube to retard air intake into the reservoir and retard leaking of liquid from the reservoir when pressure is not applied to the pump.

4. The toothbrush system of claim 3, wherein the check valve is inserted into the outlet.

5. The toothbrush system of claim 1, wherein the first liquid is tooth whitening product or gel.

6. The toothbrush system of claim 1, comprising a second replaceable reservoir cartridge retaining a second liquid, the second replaceable reservoir cartridge comprising a second funneling shaped extension, an second outlet defined in a forward end of the second funneling shaped extension, a second sealing material covering the second outlet, and a second pump for displacing the second liquid into the functional end of the toothbrush, wherein the second replaceable cartridge is configured to be removably inserted into the cartridge recess with the second funneling shaped extension inserted into the flared portion of the recess and the connection tube extending through the second sealing material into the funneling shaped extension, wherein the first liquid has a different composition that the second liquid.

* * * * *